(12) United States Patent
Green, Jr. et al.

(10) Patent No.: US 10,529,443 B2
(45) Date of Patent: Jan. 7, 2020

(54) METHODS FOR GENOME ASSEMBLY AND HAPLOTYPE PHASING

(71) Applicant: The Regents of the University of California, Oakland, CA (US)

(72) Inventors: Richard E. Green, Jr., Santa Cruz, CA (US); Liana F. Lareau, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/202,042

(22) Filed: Nov. 27, 2018

(65) Prior Publication Data

US 2019/0147978 A1    May 16, 2019

Related U.S. Application Data

(63) Continuation of application No. 15/900,723, filed on Feb. 20, 2018, which is a continuation of application No. 15/167,880, filed on May 27, 2016, now Pat. No. 9,910,955, which is a continuation of application No. 14/170,339, filed on Jan. 31, 2014, now Pat. No. 9,411,930.

(60) Provisional application No. 61/759,941, filed on Feb. 1, 2013.

(51) Int. Cl.
   *C12Q 1/68* (2018.01)
   *G16B 30/00* (2019.01)
   *C12Q 1/6874* (2018.01)

(52) U.S. Cl.
   CPC .......... *G16B 30/00* (2019.02); *C12Q 1/6874* (2013.01)

(58) Field of Classification Search
   CPC . C12Q 1/6874; C12Q 2523/101; G16B 30/00
   See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,988,617 A | 1/1991 | Landergren et al. |
| 5,143,854 A | 9/1992 | Pirrung et al. |
| 5,234,809 A | 8/1993 | Boom et al. |
| 5,242,794 A | 9/1993 | Whiteley et al. |
| 5,348,853 A | 9/1994 | Wang et al. |
| 5,476,930 A | 12/1995 | Letsinger et al. |
| 5,494,810 A | 2/1996 | Barany et al. |
| 5,567,583 A | 10/1996 | Wang et al. |
| 5,571,639 A | 11/1996 | Hubbell et al. |
| 5,593,839 A | 1/1997 | Hubbell et al. |
| 5,705,628 A | 1/1998 | Hawkins |
| 5,780,613 A | 7/1998 | Letsinger et al. |
| 5,786,146 A | 7/1998 | Herman et al. |
| 5,837,832 A | 11/1998 | Chee et al. |
| 5,989,823 A | 11/1999 | Jayasena et al. |
| 5,994,056 A | 11/1999 | Higuchi |
| 6,033,854 A | 3/2000 | Kumit et al. |
| 6,110,709 A | 8/2000 | Aubel et al. |
| 6,117,635 A | 9/2000 | Nazarenko et al. |
| 6,171,785 B1 | 1/2001 | Higuchi |
| 6,174,670 B1 | 1/2001 | Wittwer et al. |
| 6,225,109 B1 | 5/2001 | Juncosa et al. |
| 6,287,766 B1 | 9/2001 | Nolan et al. |
| 6,326,145 B1 | 12/2001 | Whitcombe et al. |
| 6,449,562 B1 | 9/2002 | Chandler et al. |
| 6,582,938 B1 | 6/2003 | Su et al. |
| 6,787,308 B2 | 9/2004 | Balasubramanian et al. |
| 6,833,246 B2 | 12/2004 | Balasubramanian |
| 6,897,023 B2 | 5/2005 | Fu et al. |
| 6,969,488 B2 | 11/2005 | Bridgham et al. |
| 7,001,724 B1 | 2/2006 | Greenfield |
| 7,361,468 B2 | 4/2008 | Liu et al. |
| 7,414,117 B2 | 8/2008 | Saito et al. |
| 7,425,415 B2 | 9/2008 | Pfeifer et al. |
| 7,709,179 B2 | 5/2010 | Iwashita |
| 7,901,891 B2 | 3/2011 | Drmanac |
| 7,985,546 B2 | 7/2011 | Church et al. |
| 8,058,004 B2 | 11/2011 | Oleinikov |
| 8,076,070 B2 | 12/2011 | Chen et al. |
| 8,153,373 B2 | 4/2012 | De Laat et al. |
| 8,278,112 B2 | 10/2012 | Shokat et al. |

(Continued)

FOREIGN PATENT DOCUMENTS

| | | |
|---|---|---|
| EP | 476014 A1 | 3/1992 |
| EP | 717113 A2 | 6/1996 |

(Continued)

OTHER PUBLICATIONS

Tanizawa, et al. "Mapping of long-range associations throughout the fission yeast genome reveals global genome organization linked to transcriptional regulation," Nucleic Acids Research, 2010, 38: 8164-8177.

Teague, et al. "High-resolution human genome structure by single-molecule analysis." Proceedings of the National Academy of Sciences. 2010, 107(24): 10848-10853.

Tyagi, et al., "Molecular beacons: probes that fluoresce upon hybridization," Nature biotechnology, 1996, 14: 303-308.

Umbarger, M.A., "Chromosome conformation capture assays in bacteria", Methods, 58, 2012, pp. 212-220.

Venter, et al., "The sequence of the human genome," Science, Feb. 16, 2001, 291:1304-51.

(Continued)

*Primary Examiner* — David C Thomas
(74) *Attorney, Agent, or Firm* — Gavrilovich, Dodd & Lindsey LLP

(57) ABSTRACT

The disclosure provides methods to assemble genomes of eukaryotic or prokaryotic organisms. The disclosure further provides methods for haplotype phasing and meta-genomics assemblies.

38 Claims, 3 Drawing Sheets

(56) References Cited

U.S. PATENT DOCUMENTS

| | | | |
|---|---|---|---|
| 9,411,930 B2* | 8/2016 | Green, Jr. | G16B 30/00 |
| 9,910,955 B2* | 3/2018 | Green, Jr. | G16B 30/00 |
| 2002/0012930 A1 | 1/2002 | Rothberg et al. | |
| 2002/0190663 A1 | 12/2002 | Rasmsen | |
| 2003/0022207 A1 | 1/2003 | Balasubramanian et al. | |
| 2003/0044781 A1 | 3/2003 | Korlach et al. | |
| 2003/0064398 A1 | 4/2003 | Barnes | |
| 2003/0068629 A1 | 4/2003 | Rothberg et al. | |
| 2003/0100102 A1 | 5/2003 | Rothberg et al. | |
| 2003/0148344 A1 | 8/2003 | Rothberg et al. | |
| 2004/0106110 A1 | 6/2004 | Balasubramanian et al. | |
| 2004/0248161 A1 | 12/2004 | Rothberg et al. | |
| 2005/0079510 A1 | 4/2005 | Berka et al. | |
| 2005/0100932 A1 | 5/2005 | Lapid et al. | |
| 2005/0124022 A1 | 6/2005 | Srinivasan et al. | |
| 2005/0130161 A1 | 6/2005 | Fraser et al. | |
| 2006/0012784 A1 | 1/2006 | Ulmer | |
| 2006/0012793 A1 | 1/2006 | Harris | |
| 2006/0024678 A1 | 2/2006 | Buzby | |
| 2006/0024711 A1 | 2/2006 | Lapid et al. | |
| 2006/0078909 A1 | 4/2006 | Srinivasan et al. | |
| 2006/0078937 A1 | 4/2006 | Korlach et al. | |
| 2009/0111115 A1 | 4/2009 | Drmanac et al. | |
| 2010/0062947 A1 | 3/2010 | De Laat et al. | |
| 2010/0093986 A1 | 4/2010 | Zwick et al. | |
| 2010/0130373 A1 | 5/2010 | Dekker et al. | |
| 2011/0033854 A1 | 2/2011 | Drmanac et al. | |
| 2011/0287947 A1 | 11/2011 | Chen et al. | |
| 2012/0197533 A1 | 8/2012 | Nazarenko et al. | |
| 2012/0302449 A1 | 11/2012 | Dong et al. | |
| 2013/0096009 A1* | 4/2013 | Dekker | C12Q 1/6837 506/2 |
| 2013/0183672 A1* | 7/2013 | de Laat | C12Q 1/6855 435/6.11 |

FOREIGN PATENT DOCUMENTS

| | | |
|---|---|---|
| EP | 728520 A1 | 8/1996 |
| WO | 90/15070 A1 | 12/1990 |
| WO | 92/10092 A1 | 6/1992 |
| WO | 93/09668 A1 | 5/1993 |
| WO | 95/11995 A1 | 5/1995 |
| WO | 97/29212 A1 | 8/1997 |
| WO | 98/041651 A1 | 9/1998 |
| WO | 02/088382 A2 | 11/2002 |
| WO | 02/103046 A2 | 12/2002 |
| WO | 03/020968 A2 | 3/2003 |
| WO | 03/031947 A2 | 4/2003 |
| WO | 05/005655 A1 | 1/2005 |
| WO | 05/005657 A1 | 1/2005 |
| WO | 05/044836 A2 | 5/2005 |
| WO | 08/024473 A2 | 2/2008 |
| WO | 09/053039 A1 | 4/2009 |
| WO | 12/047726 A1 | 4/2012 |
| WO | 2012/106546 A2 | 8/2012 |
| WO | 2012/142531 A2 | 10/2012 |
| WO | 12/150317 A1 | 11/2012 |

OTHER PUBLICATIONS

Whitcombe, et al., "Detection of PCR Products Using Self-probing Amplicons and Fluorescence," Nature Biotechnology,1999, 17:804-807.

Wing, et al., "An improved method of plant megabase DNA isolation in agarose microbeads suitable for physical mapping and YAC cloning," The Plant Journal, 1993, 4(5): 893-898.

Zhou, et al., "A single molecule scaffold for the maize genome," PLoS Genetics, 2009, 5(11): e1000711.

Adams et al., "The Genome Sequence of Drosophila melanogaster," Science, Mar. 24, 2000, 287.5461: 2185-2195.

Bansal et al., "Hapcut: an efficient and accurate algorithm for the haplotype assembly problem," Bioinformatics, 2006, 24(16): i153-i159.

Barz, Wolfgang, Extended European Search Report, Application No. 14745949.9, European Patent Office, dated Nov. 21, 2016.

Cai et al., "SATB1 packages densely looped transcriptionally active chromatin for coordinated expression of cytokine genes," Nature Genetics, 2006, 38.11: 1278-1288.

Chapman et al., "Meraculo: de novo genome assembly with short paired-end reads," PloS one, 2011, 6.8: e23501.

Constans A., "Microarrays in Microtubes," Scientist. 2003 17.13: 36.

Cortese J. , "Array of options," Scientist, 2000 14.11: 26.

Cortese J., "The array of today," Scientist, 2000 14.17: 25.

Dekker et al., "Capturing chromosome conformation," Science, 2002, 295:1306-1311.

Dostie et al., "Chromosome Conformation Capture Carbon Copy (5C): a massively parallel solution for mapping interactions between genomic elements," Genome research, 2006, 16.10: 1299-1309.

Drmanac et al., "Human Genome Sequencing Unchained Base Reads on Self-Assembling DNA Nanoarrays," Science, Jan. 1, 2010, 327.5961: 78-81.

Eakins et al., "Microarrays: their origins and applications," Trends in Biotechnology, 1999, 17: 217-218.

Fan et al. "A versatile assay for high-throughput gene expression profiling on universal array matrices." Genome Research, 2004, 14.5: 878-885.

Fangman et al., "Activation of replication origins within yeast chromosomes," Annual Review of Cell Biology, 1991 7.1: 375-402.

Fodor et al., "Light-directed spatially addressable parallel chemical synthesis," Science, Feb. 15, 1991 , 251.4995: 767-773.

Fyodorov et al., "Chromatin assembly in vitro with purified recombinant ACF and NAP-1," Methods in Enzymology, 2002, 371: 499-515.

Garaj et al., "Graphene as a sub-nanometer trans-electrode membrane," Nature, Sep. 9, 2010, 467(7312): 190-193.

Gilmour et al., "Detecting protein-DNA interactions in vivo: distribution of RNA polymerase on specific bacterial genes." Proceedings of the National Academy of Sciences, 1984, 81:4275-4279.

Gwynne et al., "Microarray analysis: the next revolution in molecular biology," Science, Aug. 6, 1999.

Heid et al., "Real time quantitative PCR," Genome Research, 1996: 6(10): 986-994.

Herschleb et al., "Pulsed-field gel electrophoresis," Nat Protoc., 2007, 2(3): 677-84.

Kalhor et al., "Genome architectures revealed by tethered chromosome conformation capture and population-based modeling," Nature Biotechnology, 2012, 30(1): 90-98.

Kitzman et al., "Haplotype-resolved genome sequencing of a Gujarati Indian individual," Nature Biotechnology, 2011, 29(1): 59-63.

Kundu et al., "Activator-dependent transcription from chromatin in vitro involving targeted histone acetylation by p300," Molecular Cell, 2000, 6(3): 551-561.

Lasken et al., "Mechanism of chimera formation during the Multiple Displacement Amplification reaction," BMC Biotechnology, 2007, 7(1): 19.

Lemieux et al., "Overview of DNA chip technology," Molecular Breeding, 1998, 4(4): 277-289.

Levene et al., "Zero-Mode Waveguides for Single-Molecule Analysis at High Concentrations," Science, Jan. 31, 2003, 299: 682-686.

Lieberman-Aiden et al. "Comprehensive mapping of long range interactions reveals folding principles of the human genome." Science, Oct. 9, 2009; 326:289-293.

Lupski et al., "Whole-genome sequencing in a patient with Charcot—Marie—Tooth neuropathy," New England Journal of Medicine, 2010, 362:1181-1191.

Lusser et al., "Strategies for the reconstitution of chromatin." Nature Methods. 2004 1(1): 19-26.

MA et al., "Application of Real-time Polymerase Chain Reaction (RT-PCR)", The Journal of American Science, 2006, 2(3):1-15.

Maniatis et al., Molecular Cloning: A Laboratory Manual Cold Spring Harbor N.Y. pp. 280-281 (1982).

Margulies et al., Genome Sequencing in Open Microfabricated High Density Picoliter Reactors, Nature, Sep. 15, 2005; 437(7057): 376-380.

(56) References Cited

OTHER PUBLICATIONS

Marshall et al., "DNA chips: an array of possibilities.," Nat Biotechnol. ,Jan. 1998, 16:27-31.
Mary, Isabelle et al., "Metaproteomic and metagenomic analyses of defined oceanic microbial populations using microwave cell fixation and flow cytometric sorting", FEMS Microbiol. Ecol., 74, 2010, pp. 10-18.
Nazarenko et al., "A closed tube format for amplification and detection of DNA based on energy transfer," Nucleic acids research, 1997 25(12): 2516-2521.
Peng et al., "Generation of long insert pairs using a Cre-LoxP Inverse PCR approach," PLoS One, 2012, 7(1): e29437.
Peters et al., "Accurate whole-genome sequencing and haplotyping from 10 to 20 human cells", Nature, vol. 487, No. 7406, Jul. 11, 2012, pp. 190-195.
Rios et al., "Identification by whole-genome resequencing of gene defect responsible for severe hypercholesterolemia," Human Molecular Genetics., 2010, 19(22): 4313-4318.
Sambrook et al., "Mixed Oligonucleotide-primed Amplification of cDNA (MOPAC)," Cold Spring Harbor Protocols, 2006.
Schena et al., "Genes genomes and chips," DNA microarrays: A practical approach. 1999 : 1-15.
Schena et al. Parallel analysis with biological chips. PCR applications: protocols for functional genomics. 1999 : 445-456.
Schena M. (ed.), Microarray Biochip Technology (2000), ISBN-10: 1881299376 | ISBN-13: 978-1881299370.
Schwartz et al., "Separation of yeast chromosome-sized DNAs by pulsed field gradient gel electrophoresis," Cell, 1984, 37: 67-75.
Sewards, Richard, Combined Search and Examination Report under Sections 17 & 18(3), Great Britain Patent Application No. GB1520448.0, dated May 31, 2016.
Shalon et al., "A DNA microarray system for analyzing complex DNA samples using two-color fluorescent probe hybridization," Genome Research, 1996, 6: 639-645.
Simpson, et al., "Efficient de novo assembly of large genomes using compressed data structures," Genome Res., Mar. 2012, 22(3): 549-556.
Solomon et al., "Mapping protein-DNA interactions in vivo with formaldehyde: evidence that histone H4 is retained on a highly transcribed gene," Cell, 1988, 53(6):937-947.
Solomon et al., "Formaldehyde-mediated DNA-protein crosslinking: a probe for in vivo chromatin structures." Proceedings of the National Academy of Sciences, 1985, 82: 6470-6474.
Soni, et al., "Progress toward ultrafast DNA sequencing using solid-state nanopores," Clin Chem., Nov. 2007, 53: 1996-2001. Epub Sep. 21, 2007.
Fang et al., "Mapping of long-range chromatin interactions by proximity ligation-assisted ChIP-seq", Cell Research, 2016, 26:1345-1348.
Fullwood et al., "An oestrogen-receptor-a-bound human chromatin interactome", Nature, vol. 462, Nov. 5, 2009, pp. 58-64.
Hsieh et al., "Mapping Nucleosome Resolution Chromosome Folding in Yeast by Micro-C", Cell, 2015, 162,108-119.
Juric et al., "MAPS: Model-based analysis of long-range chromatin interactions from PLAC-seq and HiChIP experiments", PLOS Computational Biology, Apr. 14, 2019, https://doi.org/10.1371/journal.pcbi.1006982, pp. 1-24.
Krietenstein et al., "Ultrastructural details of mammalian chromosome architecture", bioRxiv preprint first posted online May 17, 2019; doi: http://dx.doi.org/10.1101/639922.
Li et al., "Simultaneous profiling of DNA methylation and chromatin architecture in mixed populations and in single cell", bioRxiv preprint first posted online Nov. 14, 2018; doi: http://dx.doi.org/10.1101/470963.
Li et al., "OCEAN-C: mapping hubs of open chromatin interactions across the genome reveals gene regulatory networks", Genome Biology, 2018, 19:54.
Ma et al., "Fine-scale chromatin interaction maps reveal the cis-regulatory landscape of human lincRNA genes", Nature Methods, Rcvd. Sep. 3, 2014, Accepted. Oct. 17, 2014, Published Online Dec. 1, 2014, pp. 1-14.
Ma et al., "Using DNase Hi-C techniques to map global and local three-dimensional genome architecture at high resolutin", bioRxiv preprint first posted online Sep. 5, 2017; doi: http://dx.doi.org/10.1101/184846.
Mifsud et al., "Mapping long-range promoter contacts in human cells with high-resolution capture Hi-C", Nature Genetics, 2015, vol. 47 (6), pp. 598-609.
Ramani et al., "Mapping 3D genome architecture through in situ DNase Hi-C", Nature Protocols, vol. 11, No. 11, 2016, pp. 2104-2121.
Ramani et al., "Massively multiplex single-cell Hi-C", Nat Methods, Mar. 2017, 14(3):263-266.
Rao et al., "A 3D Map of the Human Genome at Kilobase Resolution Reveals Principles of Chromatin Looping", Cell, Dec. 18, 2014, 159, pp. 1665-1680.
Schmitt et al., "A Compendium of Chromatin Contact Maps Reveals Spatially Active Regions in the Human Genome", Cell Reports, Nov. 15, 2016, 17, 2042-2059.
Wang et al., "The 3D Genome Browser: a web-based browser for visualizing 3D genome organization and long-range chromatin interactions", Genome Biology, 2018, 19:151.
Burton et al., "Chromosome-scale scaffolding of de novo genome assemblies based on chromatin interactions", Nature Biotechnology, vol. 31, No. 12, Dec. 2013, pp. 1119-1127.
Helliot, Bertrand, Office Action, Application No. 14745949.9, European Patent Office, dated Aug. 19, 2019.

\* cited by examiner

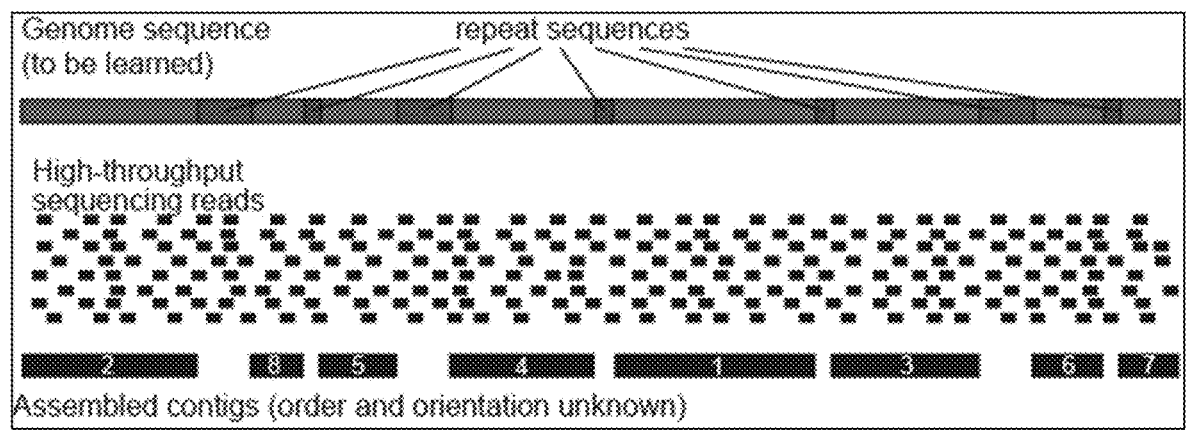
FIGURE 1
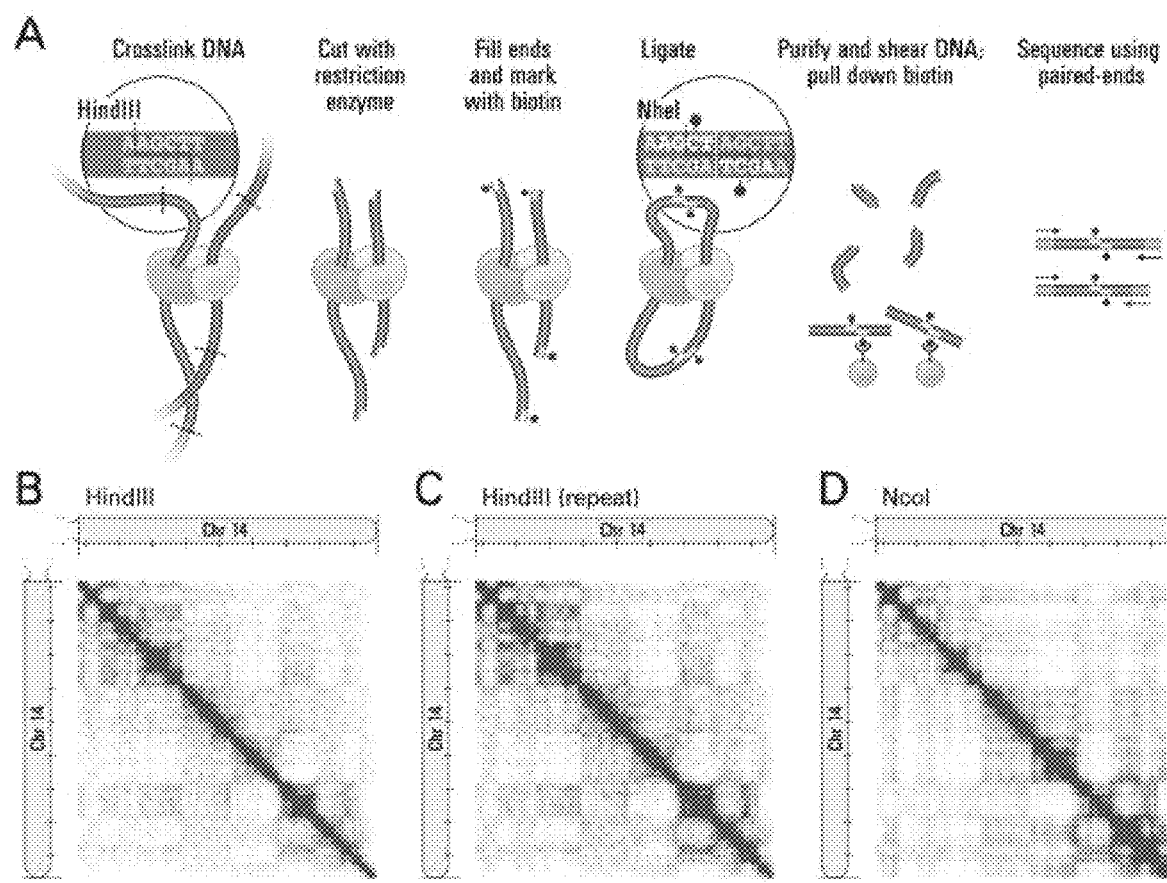
FIGURE 2A-D

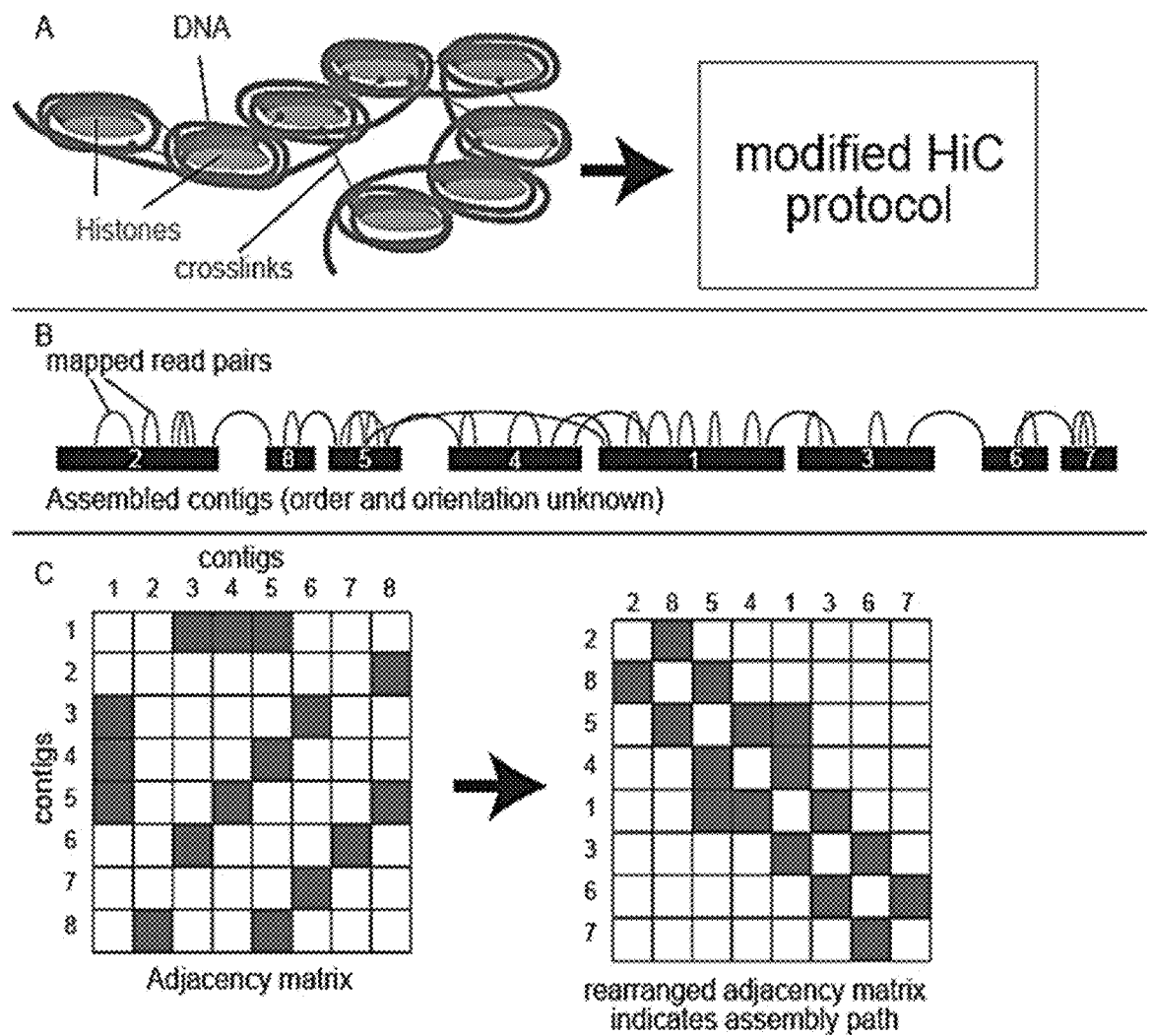
FIGURE 4A-C

METHODS FOR GENOME ASSEMBLY AND HAPLOTYPE PHASING

CROSS REFERENCE TO RELATED APPLICATIONS

This application is a continuation of U.S. patent application Ser. No. 15/900,723, filed Feb. 20, 2018, which is a continuation of U.S. patent application Ser. No. 15/167,880, filed May 27, 2016, now U.S. Pat. No. 9,910,955, which is a continuation of U.S. patent application Ser. No. 14/170,339, filed Jan. 31, 2014, now U.S. Pat. No. 9,411,930, which application claims priority under 35 U.S.C. § 119 from Provisional Application Ser. No. 61/759,941, filed Feb. 1, 2013, the disclosures of which are incorporated herein by reference.

TECHNICAL FIELD

The disclosure provides for methods of genome assembly and haplotype phasing for identifying short, intermediate and long term connections within a genome.

BACKGROUND

It remains difficult in theory and in practice to produce high-quality, highly contiguous genome sequences.

SUMMARY

The disclosure provides methods for accelerating and improving de novo genome assembly. The methods disclosed herein utilize methods for data analysis that allow for rapid and inexpensive de novo assembly of genomes from one or more subjects. The disclosure further provides that the methods disclosed herein can be used in a variety of applications, including haplotype phasing, and metagenomics analysis.

In a certain embodiment, the disclosure provides for a method for genome assembly comprising the steps of: generating a plurality of contigs; generating a plurality of read pairs from data produced by probing the physical layout of chromosomes, chromatin, or reconstituted chromatin; mapping or assembling the plurality of read pairs to the plurality of contigs; constructing an adjacency matrix of contigs using the read-mapping or assembly data; and analyzing the adjacency matrix to determine a path through the contigs that represent their order and/or orientation to the genome. In a further embodiment, the disclosure provides that each read pair is weighted by taking a function of each read's distance to the edge of the contig so as to incorporate information about which read pairs indicate short-range contacts and which read pairs indicate longer-range contacts. In another embodiment, the adjacency matrix can be re-scaled to down-weight the high number of contacts on some contigs that represent promiscuous regions of the genome, such as conserved binding sites for one or more agents that regulate the scaffolding interactions of chromatin, like transcriptional repressor CTCF. In another embodiment, the disclosure provides for a method for the genome assembly of a human subject, whereby the plurality of contigs is generated from the human subject's DNA, and whereby the plurality of read pairs is generated from analyzing the human subject's chromosomes, chromatin, or reconstituted chromatin made from the subject's naked DNA.

In a further embodiment, the disclosure provides that a plurality of contigs can be generated by using a shotgun sequencing method comprising: fragmenting long stretches of a subject's DNA into random fragments of indeterminate size; sequencing the fragments using high throughput sequencing methods to generate a plurality of sequencing reads; and assembling the sequencing reads so as to form a plurality of contigs.

In a certain embodiment, the disclosure provides that a plurality of read pairs can be generated by probing the physical layout of chromosomes, chromatin, or reconstituted chromatin using a Hi-C based technique. In a further embodiment, the Hi-C based technique comprises, cross-linking chromosomes, chromatin, or reconstituted chromatin with a fixative agent, such as formaldehyde, to form DNA-protein cross links; cutting the cross-linked DNA-Protein with one or more restriction enzymes so as to generate a plurality of DNA-protein complexes comprising sticky ends; filling in the sticky ends with nucleotides containing one or more markers, such as biotin, to create blunt ends that are then ligated together; fragmenting the plurality of DNA-protein complexes into fragments; pulling down junction containing fragments by using the one or more of the markers; and sequencing the junction containing fragments using high throughput sequencing methods to generate a plurality of read pairs. In a further embodiment, the plurality of read pairs for the methods disclosed herein is generated from data produced by probing the physical layout of chromatin.

In a particular embodiment, the disclosure provides that a plurality of read pairs can be determined by probing the physical layout of chromosomes or chromatin isolated from cultured cells or primary tissue. In an alternate embodiment, the plurality of read pairs can be determined by probing the physical layout of reconstituted chromatin formed by complexing naked DNA obtained from a sample of one or more subjects with isolated histones.

In another embodiment, the disclosure provides a method to determine haplotype phasing comprising a step of identifying one or more sites of heterozygosity in the plurality of read pairs, wherein phasing data for allelic variants can be determined by identifying read pairs that comprise a pair of heterozygous sites.

In a certain embodiment, the disclosure provides a method for high-throughput bacterial genome assembly, comprising a step of generating a plurality of read pairs by probing the physical layout of a plurality of microbial chromosomes using a modified Hi-C based method, comprising the modified steps of: collecting microbes from an environment; adding a fixative agent, such as formaldehyde, so as to form cross-links within each microbial cell, and wherein read pairs mapping to different contigs indicate which contigs are from the same species.

INCORPORATION BY REFERENCE

All publications, patents, and patent applications mentioned in this specification are herein incorporated by reference to the same extent as if each individual publication, patent, or patent application was specifically and individually indicated to be incorporated by reference. All publications, patents, and patent applications mentioned in this specification are herein incorporated by reference in its entirety as well as any references cited therein.

BRIEF DESCRIPTION OF THE DRAWINGS

The novel features of the disclosure are set forth with particularity in the appended claims. A better understanding of the features and advantages of the disclosure will be obtained by reference to the following detailed description that sets forth illustrative embodiments, in which the principles of the disclosure are utilized, and the accompanying drawings of which:

FIG. 1 presents an illustration of genome assembly using high-throughput sequencing reads. The genome to be assembled is shown (top). Typically, genomes have many repeat sequences that are difficult to assemble. Random, high-throughput sequence data from genomes (middle) are collected and assembled into "contigs" in regions that are unique in the genome (bottom). Contig assembly generally stops at the many repeat sequences. The final output is a set of thousands of contigs whose order and orientation relative to one another are not known. In the figure, they are arbitrarily numbered from longest to shortest.

FIG. 2A-D illustrates a Hi-C based protocol of the disclosure: (A) demonstrates where DNA is cross-linked and processed to created biotinylated junction fragments for sequencing; and (B-D) provide contact map data on human chr14 for a variety of restriction enzymes. As shown, most contacts are local along the chromosome.

FIG. 4A-C provides a method of the disclosure using Hi-C sequence data to assist genome assembly: (A) illustrates where DNA is cross-linked and processed using a Hi-C based protocol; (B) demonstrates where read-pair data is mapped to assembled contigs, generated from random shotgun sequencing and assembly; and (C) illustrates that after filtering and weighting, an adjacency matrix summarizing all inter-contig read pair data can be constructed. This matrix can be re-ordered to indicate the correct assembly path. As shown, most of the read pairs will map within a contig. From which, it is possible to learn the distribution of contact distances (e.g., see FIG. 3). Read pairs that map to different contigs provide data about which contigs are adjacent in a correct genome assembly.

DETAILED DESCRIPTION

Figure 3:
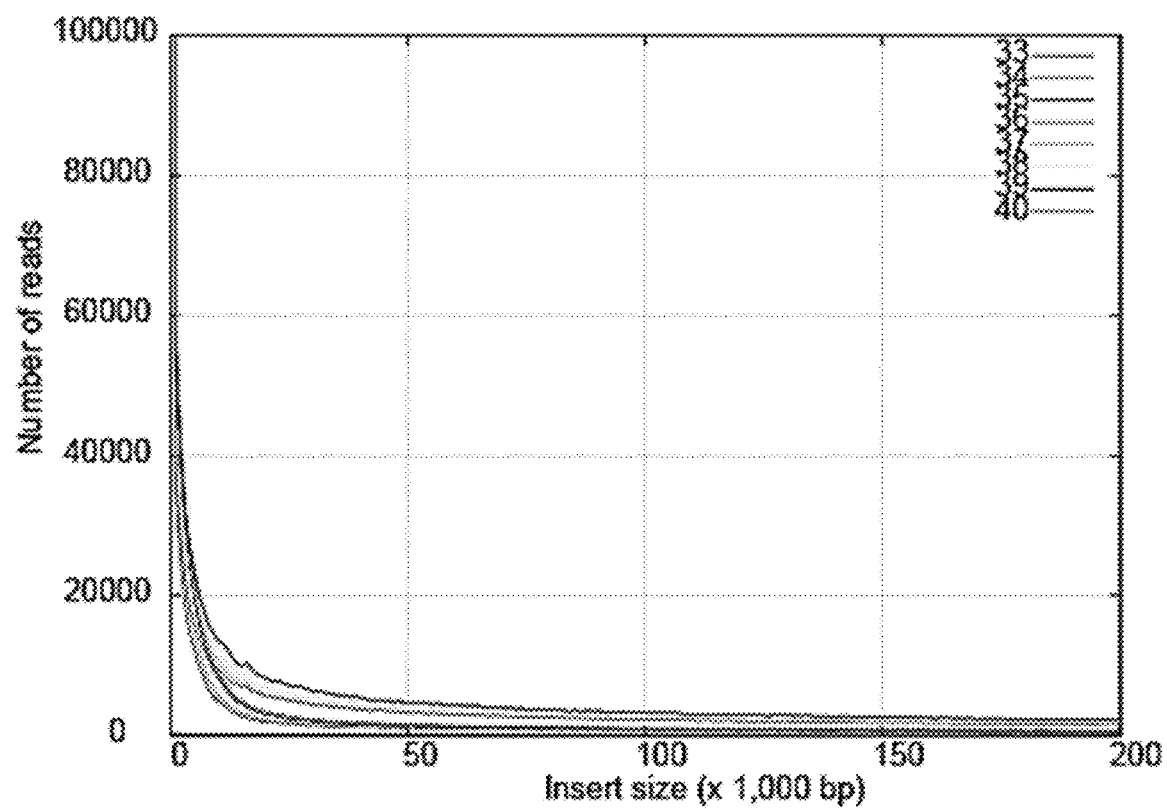
FIG. 3 provides a tracing of the distribution of intra-chromosomal read-pair distances using a Hi-C based protocol of the disclosure. Eight datasets are shown. In each dataset, the frequency of read-pairs decreases exponentially with increasing distance such that read pairs are more likely to be separated by a smaller distance than a longer distance. As shown, there is a long tail of read-pair distances that extends over hundreds of kilobases.

As used herein and in the appended claims, the singular forms "a," "and," and "the" include plural referents unless the context clearly dictates otherwise. Thus, for example, reference to "contig" includes a plurality of such contigs and reference to "probing the physical layout of chromosomes" includes reference to one or more methods for probing the physical layout of chromosomes and equivalents thereof known to those skilled in the art, and so forth.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The term "sequencing read" as used herein, refers to a fragment of DNA in which the sequence has been determined.

The term "contigs" as used herein, refers to contiguous regions of DNA sequence. "Contigs" can be determined by any number methods known in the art, such as, by comparing sequencing reads for overlapping sequences, and/or by comparing sequencing reads against a databases of known sequences in order to identify which sequencing reads have a high probability of being contiguous.

The term "subject" as used herein can refer to any eukaryotic or prokaryotic organism.

The term "naked DNA" as used herein refers to DNA that is substantially free of complexed proteins.

The term "reconstituted chromatin" as used herein refers to forming chromatin by complexing isolated nuclear proteins to naked DNA.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Basic evolutionary and biomedical research is being driven by technological advances in high-throughput sequencing. Whereas whole genome sequencing and assembly used to be the provenance of large genome sequencing centers, commercially available sequencers are now inexpensive enough that most research universities have one or several of these machines. It is now relatively inexpensive to generate massive quantities of DNA sequence data. However it remains difficult in theory and in practice to produce high-quality, highly contiguous genome sequences with current technology. Furthermore, because most organisms that one would care to analyze, including humans, are diploid, each individual has two copies of the genome. At sites of heterozygosity (where the allele given by the mother differs from the allele given by the father), it is difficult to know which sets of alleles came from which parent (known as haplotype phasing). This information can be used for many kinds of evolutionary and biomedical studies such as disease and trait association studies.

The disclosure provides methods for genome assembly that combine technologies for DNA preparation with paired-end sequencing for high-throughput discovery of short, intermediate and long term connections within a given genome. The disclosure further provides methods using these connections to assist in genome assembly, for haplotype phasing, and/or for metagenomic studies. While the methods presented herein can be used to determine the assembly of a subject's genome, it should also be understood that the methods presented herein can also be used to determine the assembly of portions of the subject's genome such as chromosomes, or the assembly of the subject's chromatin of varying lengths.

In a particular embodiment, the disclosure provides for one or more methods disclosed herein that comprise the step of generating a plurality of contigs from sequencing fragments of target DNA obtained from a subject. Long stretches of target DNA can be fragmented by cutting the DNA with one or more restriction enzymes, shearing the DNA, or a combination thereof. The resulting fragments can be sequenced using high throughput sequencing methods to obtain a plurality of sequencing reads. Examples of high throughput sequencing methods which can be used with the methods of the disclosure include, but are not limited to, 454 pyrosequencing methods developed Roche Diagnostics, "clusters" sequencing methods developed by Illumina, SOLiD and Ion semiconductor sequencing methods developed by Life Technologies, and DNA nanoball sequencing methods developed by Complete Genomics. Overlapping ends of different sequencing reads can then be assembled to form a contig. Alternatively, fragmented target DNA can be cloned into vectors. Cells or organisms are then transfected with the DNA vectors to form a library. After replicating the transfected cells or organisms, the vectors are isolated and sequenced to generate a plurality of sequencing reads. The overlapping ends of different sequencing reads can then be assembled to form a contig.

As shown in FIG. 1, genome assembly, especially with high-throughput sequencing technology can be problematic. Often, the assembly consists of thousands or tens of thousands of short contigs. The order and orientation of these contigs is generally unknown, limiting the usefulness of the genome assembly. Technologies exist to order and orient these scaffolds, but they are generally expensive, labor intensive, and often fail in discovering very long range interactions.

As will be appreciated by those in the art, samples comprising target DNA used to generate contigs can be obtained from a subject by any number of means, including by taking bodily fluids (e.g., blood, urine, serum, lymph, saliva, anal and vaginal secretions, perspiration and semen), taking tissue, or by collecting cells/organisms. The sample obtained may be comprised of a single type of cell/organism, or may be comprised multiple types of cells/organisms. The DNA can be extracted and prepared from the subject's sample using known techniques. For example, the sample may be treated to lyse a cell comprising the polynucleotide, using known lysis buffers, sonication techniques, electroporation, and the like. The target DNA may be further purified to remove contaminants, such as proteins, by using alcohol extractions, cesium gradients, and/or column chromatography.

In a particular embodiment, the disclosure provides for one or more methods disclosed herein that comprise the step of probing the physical layout of chromosomes within living cells. Examples of techniques to probe the physical layout of chromosomes through sequencing include the "C" family of techniques, such as chromosome conformation capture ("3C"), circularized chromosome conformation capture ("4C"), carbon-copy chromosome capture ("5C"), and Hi-C based methods; and ChIP based methods, such as ChIP-loop, ChIP-PET. In a certain embodiment, one or more methods disclosed herein utilize Hi-C based techniques to probe the physical layout of chromosomes, chromatin, or reconstituted chromatin.

A Hi-C based technique is summarized in FIG. 2. In brief, cross-links are created between genome regions that are in close physical proximity. Crosslinking of proteins (such as histones) to the DNA within chromatin can be accomplished according to various methods. One approach is to expose the chromatin to ultraviolet irradiation. Other approaches utilize chemical crosslinking agents. Suitable chemical crosslinking agents include, but are not limited to, formaldehyde and psoralen. The DNA may be immunoprecipitated prior to or after crosslinking. Such methods generally involve fragmenting chromatin and then contacting the fragments with an antibody that specifically recognizes and binds to acetylated histones, particularly H3. Examples of such antibodies include, but are not limited to, Anti Acetylated Histone H3, available from Upstate Biotechnology, Lake Placid, N.Y. The polynucleotides from the immunoprecipitate can subsequently be collected from the immunoprecipitate. Prior to fragmenting the chromatin, one can optionally crosslink the acetylated histones to adjacent DNA. The mixture is then treated to fractionate polynucleotides in the mixture. Fractionation techniques are known in the art and include, for example, shearing techniques to generate smaller genomic fragments. Fragmentation can be accomplished using established methods for fragmenting chromatin, including, for example, sonication, shearing and/or the use of restriction enzymes. The resulting fragments can vary in size. In one embodiment, using sonication techniques, fragments of approximately 200-400 nucleotides can be obtained. Then, a series of steps is performed that creates a single, short stretch of DNA that is a ligation product between the two regions that were originally in close physical proximity. These ligation products are then subjected to paired-end sequencing (the beginning and end of each fragment is sequenced) using high-throughput sequencing. Each read pair represents a single pair of genomic regions that were in close physical proximity.

One feature of the data generated by Hi-C is that most reads pairs, when mapped back to the genome, are found to be in close linear proximity. That is, most read pairs are found to be close to one another in the genome. In detecting long-range intra-chromosomal and especially inter-chromosomal contacts, this "background" of short and intermediate range intra-chromosomal contacts are background noise to be factored out using Hi-C analysis.

Examination of the physical distance between intra-chromosomal read pairs indicates several useful features of the data with respect to genome assembly. First, shorter range interactions are more common than longer-range interactions (e.g., see FIG. 3). That is, each read of a read-pair is more likely to be mated with a region close by in the actual genome than it is to be with a region that is far away. Second, there is a long tail of intermediate and long-range interactions. That is, read-pairs carry information about intrachromosomal arrangement at megabase (Mb) distances. These features of the data simply indicate that regions of the genome that are nearby on the same chromosome are more likely to be in close physical proximity—an expected result because they are chemically linked to one another through the DNA backbone.

Universally, procedures for probing the physical layout of chromosomes, such as Hi-C based techniques, utilize chromatin that is formed within a cell/organism, such as chromatin isolated from cultured cells or primary tissue. The disclosure provides not only for the use of such techniques with chromatin isolated from a cell/organism but also with reconstituted chromatin. Reconstituted chromatin has many benefits over chromatin formed within a cell/organism. First, for many samples, the collection of naked DNA samples can be achieved by using a variety of noninvasive to invasive methods, such as by collecting bodily fluids, swabbing buccal or rectal areas, taking epithelial samples, etc. Moreover, it may be impractical or impossible to successfully culture certain types of cells long-term. Second, reconstituted chromatin will not have the inter-chromosomal and other long-range interactions that generate artifacts for genome assembly and haplotype phasing. Third, by varying the ratio of DNA to histones, it is possible to reduce the nucleosome density. In this way, crosslinks will naturally favor longer-range interactions. As shorter range contacts are disfavored and longer range contacts favored, the usefulness for contig ordering will be increased.

In a particular embodiment, the disclosure provides for one or more methods disclosed herein that comprise the step of mapping the plurality of read pairs to the plurality of contigs. Most of the read pairs will map within in a contig, and from which the distribution of distances between read pairs can be learned, and from which an adjacency matrix of contigs can be constructed using read pairs that map to different contigs.

In a certain embodiment, the disclosure provides for one or more methods disclosed herein that comprise the step of constructing an adjacency matrix of contigs using the read-mapping data from the read-pair data. In another embodiment, the adjacency matrix uses a weighting scheme for read pairs that incorporate the tendency for short-range interactions over long-range interactions (e.g., see FIG. 4). In a further embodiment, the adjacency matrix can further be re-scaled to down-weight the high number of contacts on some contigs that represent promiscuous regions of the genome. In yet a further embodiment, this scaling can be directed by searching for one or more conserved binding sites for one or more agents that regulate the scaffolding interactions of chromatin, such as transcriptional repressor CTCF.

In particular embodiment, the disclosure provides for one or more methods disclosed herein that comprise a step of analyzing the adjacency matrix to determine a path through the contigs that represent their order and/or orientation to the genome. In another embodiment, the path through the contigs is chosen so that each contig is visited exactly once. In a further embodiment, the path through the contigs is chosen so that edge-weighting of adjacency matrix is maximized. In yet a further embodiment, the path through the contigs is chosen so that each contig is visited exactly once and that edge-weighting of adjacency matrix is maximized.

In diploid genomes, it often important to know which allelic variants are linked on the same chromosome. This is known as the haplotype phasing. Short reads from high-throughput sequence data rarely allow one to directly observe which allelic variants are linked. Computational inference of haplotype phasing is unreliable at long distances. The disclosure provides one or methods that allow for determining which allelic variants are linked using allelic variants on read pairs.

Humans are heterozygous at an average of 1 site in 1,000. A lane of data using high throughput sequencing methods can generate about 150,000,000 read pairs. Each read pair is 100 base pairs long. From these parameters, it is estimated that one-tenth of all reads will cover a heterozygous site. Thus, on average one-hundredth of all read pairs will cover a pair of heterozygous sites. These 1,500,000 read pairs (one-hundredth of 150,000,000) provide phasing data. Because there are approximately 3 billion bases in the human genome and one in one-thousand is heterozygous, there are approximately 3 million heterozygous sites in a human genome. Each read-pair reveals phase data that covers a pair of heterozygous sites. As there are 1,500,000 such read pairs, the average coverage of each heterozygous site to be phased using high throughput sequence method accounts for one lane of data (1×) using typical high throughput sequencing machines. A genome can therefore be reliably and completely phased with one lane of Hi-C sequence data using the methods disclosed herein.

One current avenue of research, meta-genomics, investigates the DNA sequence of all organisms that inhabit a given ecological environment. Examples include random sequencing of all gut microbes, the microbes found on certain areas of skin, and the microbes that live in toxic waste sites. These studies have revealed a lot about the composition of the microbe population in these environments and embodiments of interrelated biochemistries encoded by their respective genomes. However, metagenomic studies are all hampered by the complexity of the biological environments. Generally, there are too many species with too much genome variability to attempt to assemble genomes from the random data recovered. The disclosure provides one or more methods that allow for the assembly of genomes for metagenomic projects.

The following examples are intended to illustrate but not limit the disclosure. While they are typical of those that might be used, other procedures known to those skilled in the art may alternatively be used.

EXAMPLES

Methods to Generate Chromatin In Vitro: Two approaches to reconstitute chromatin include (1) to use ATP-independent random deposition of histones onto DNA, while the other (2) uses ATP-dependent assembly of periodic nucleosomes. The disclosure allows the use of either approach with one or more methods disclosed herein. Examples of both approaches to generate chromatin can be found in Lusser et al. ("Strategies for the reconstitution of chromatin," Nature Methods (2004), 1(1):19-26), which is incorporated herein by reference in its entirety, including the references cited therein.

Genome Assembly Using HI-C Based Techniques: A genome from a human subject was fragmented into pseudo-contigs having a size of 500 kb. Using a Hi-C based method, a plurality of read pairs were generated by probing the physical layout of chromosomes within living cells. Any number of Hi-C based methods can be used to generate read pairs, including the method presented in Lieberman-Aiden et al. ("Comprehensive mapping of long range interactions reveals folding principles of the human genome," Science (2009), 326(5950):289-293), which is incorporated herein in-full, including the references cited therein. Read pairs were mapped to all pseudo-contigs and those pairs that mapped to two separate pseudo-contigs, were used to construct an adjacency matrix based upon the mapping data. Each read pair was weighted by taking a function of each read's distance to the edge of the pseudo-contig so as to mathematically incorporate the empirically known higher probability of shorter contacts than longer contacts. Then, for each pseudo-contig, the adjacency matrix was analyzed to determine a path through the pseudo-contigs by finding the single best neighbor pseudo-contig, which was determined by having the highest sum-of-weights. By performing these methods, it was found that >97% of all pseudo-contigs identified their correct neighbor. Additional experiments can be performed to test the impact of shorter contigs and alternate weighting and path-finding schemes.

Methods for Haplotype Phasing: Because the read pairs generated by the methods disclosed herein are generally derived from intra-chromosomal contacts, any read pairs that contain sites of heterozygosity will also carry information about their phasing. Using this information, reliable phasing over short, intermediate and even long (megabase) distances can be performed rapidly and accurately. Experiments designed to phase data from one of the 1000 genomes trios (a set of mother/father/offspring genomes) have reliably inferred phasing.

Methods for Meta-genomic Assembly: Microbes are collected from an environment and fixed with a fixative agent, such as formaldehyde, in order to form cross-links within each microbial cell. A plurality of contigs from each microbe is generated by using high-throughput sequencing. A plurality of read pairs are generated by using Hi-C based techniques. Read pairs that map to different contigs indicate which contigs are from the same species.

While preferred embodiments of the disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method comprising:
    contacting a sample to a stabilizing agent, said sample comprising a nucleic acid molecule complexed to at least one nucleic acid binding protein;
    cleaving the nucleic acid into a plurality of segments comprising at least a first segment and a second segment;
    attaching the first segment and the second segment at a junction;
    obtaining at least some sequence on each side of the junction to generate a first read pair;
    mapping the first read pair to a set of contigs; and
    determining a path through the set of contigs that represents an order and/or orientation to a genome, wherein the path through the set of contigs that represents an order and/or orientation to the genome is determined so that each contig is visited exactly once.

2. The method of claim 1, comprising:
    excluding the first read pair from contig assembly analysis because said at least some sequence on each side of the junction maps to a common contig; and
    determining a path through the contigs that represents an order and/or orientation to the genome using a second read pair.

3. The method of claim 1, comprising:
    contacting the sample to an antibody prior to contacting the sample to the stabilizing agent.

4. The method of claim 1, comprising:
    contacting the sample to an antibody subsequent to contacting the sample to the stabilizing agent.

5. The method of claim 1, wherein cleaving the nucleic acid into at least a first segment and a second segment comprises cutting the nucleic acid using at least one restriction enzyme.

6. The method of claim 1, wherein cleaving the nucleic acid into at least a first segment and a second segment comprises shearing the nucleic acid.

7. The method of claim 1, wherein cleaving the nucleic acid into at least a first segment and a second segment comprises sonicating the nucleic acid.

8. The method of claim 1, wherein contacting a sample to a stabilizing agent comprises administering ultraviolet light.

9. The method of claim 1, wherein contacting a sample to a stabilizing agent comprises contacting the sample to a chemical fixative.

10. The method of claim 9, wherein the chemical fixative comprises formaldehyde.

11. The method of claim 9, wherein the chemical fixative comprises psoralen.

12. The method of claim 1, wherein the at least one nucleic acid binding protein comprises a native chromatin constituent.

13. The method of claim 1, wherein the at least one nucleic acid binding protein comprises an exogenously supplied histone.

14. The method of claim 1, wherein attaching comprises filling in sticky ends using at least some biotin tagged nucleotides and ligating the blunt ends.

15. The method of claim 1, wherein determining a path through the set of contigs that represents an order and/or orientation to the genome comprises down-weighing contigs that represent promiscuous regions of the genome.

16. The method of claim 1, wherein the set of contigs is generated by a shotgun sequencing method.

17. The method of claim 1, wherein determining a path through the set of contigs that represents an order and/or orientation to the genome comprises haplotype phasing the set of contigs.

18. The method of claim 17, wherein haplotype phasing the set of contigs comprise identifying one or more sites of heterozygosity in a plurality of read pair sequences, wherein phasing data for allelic variants is determined by identifying read pairs that comprise a pair of heterozygous sites.

19. The method of claim 1, comprising excluding from analysis read pair sequence that maps to a common contig, so as to determine a path through the set of contigs that represents an order and/or orientation to the genome using read pairs that map to different contigs.

20. A method comprising:
    contacting a sample to a stabilizing agent, said sample comprising a nucleic acid molecule complexed to at least one nucleic acid binding protein;
    cleaving the nucleic acid into a plurality of segments comprising at least a first segment and a second segment;
    attaching the first segment and the second segment at a junction;
    obtaining at least some sequence on each side of the junction to generate a first read pair;
    mapping the first read pair to a set of contigs; and
    determining a path through the set of contigs that represents an order and/or orientation to a genome, wherein determining a path through the set of contigs that represents an order and/or orientation to the genome comprises down-weighing contigs that represent promiscuous regions of the genome.

21. The method of claim 20, comprising:
    excluding the first read pair from contig assembly analysis because said at least some sequence on each side of the junction maps to a common contig; and
    determining a path through the contigs that represents an order and/or orientation to the genome using a second read pair.

22. The method of claim 20, comprising:
    contacting the sample to an antibody prior to contacting the sample to the stabilizing agent.

23. The method of claim 20, comprising:
    contacting the sample to an antibody subsequent to contacting the sample to the stabilizing agent.

24. The method of claim 20, wherein cleaving the nucleic acid into at least a first segment and a second segment comprises cutting the nucleic acid using at least one restriction enzyme.

25. The method of claim 20, wherein cleaving the nucleic acid into at least a first segment and a second segment comprises shearing the nucleic acid.

26. The method of claim 20, wherein cleaving the nucleic acid into at least a first segment and a second segment comprises sonicating the nucleic acid.

27. The method of claim 20, wherein contacting a sample to a stabilizing agent comprises administering ultraviolet light.

28. The method of claim 20, wherein contacting a sample to a stabilizing agent comprises contacting the sample to a chemical fixative.

29. The method of claim 28, wherein the chemical fixative comprises formaldehyde.

30. The method of claim 28, wherein the chemical fixative comprises psoralen.

31. The method of claim 20, wherein the at least one nucleic acid binding protein comprises a native chromatin constituent.

32. The method of claim 20, wherein the at least one nucleic acid binding protein comprises an exogenously supplied histone.

33. The method of claim 20, wherein attaching comprises filling in sticky ends using at least some biotin tagged nucleotides and ligating the blunt ends.

34. The method of claim 20, wherein the path through the set of contigs that represents an order and/or orientation to the genome is determined so that each contig is visited exactly once.

35. The method of claim 20, wherein the set of contigs is generated by a shotgun sequencing method.

36. The method of claim 20, wherein determining a path through the set of contigs that represents an order and/or orientation to the genome comprises haplotype phasing the set of contigs.

37. The method of claim 36, wherein haplotype phasing the set of contigs comprise identifying one or more sites of heterozygosity in a plurality of read pair sequences, wherein phasing data for allelic variants is determined by identifying read pairs that comprise a pair of heterozygous sites.

38. The method of claim 20, comprising excluding from analysis read pair sequence that maps to a common contig, so as to determine a path through the set of contigs that represents an order and/or orientation to the genome using read pairs that map to different contigs.

\* \* \* \* \*